US011419620B2

(12) United States Patent
Cooper et al.

(10) Patent No.: US 11,419,620 B2
(45) Date of Patent: Aug. 23, 2022

(54) MINIMALLY INVASIVE THROMBECTOMY

(71) Applicant: The University of Toledo, Toledo, OH (US)

(72) Inventors: Christopher J. Cooper, Perrysburg, OH (US); Mohammad H. Elahinia, Toledo, OH (US); Rajesh Gupta, Saline, MI (US); Hamdy Ibrahim, Toledo, OH (US)

(73) Assignee: The University of Toledo, Toledo, OH (US)

( * ) Notice: Subject to any disclaimer, the term of this patent is extended or adjusted under 35 U.S.C. 154(b) by 452 days.

(21) Appl. No.: 15/919,513

(22) Filed: Mar. 13, 2018

(65) Prior Publication Data

US 2018/0256177 A1 Sep. 13, 2018

Related U.S. Application Data

(63) Continuation-in-part of application No. 14/433,278, filed as application No. PCT/US2013/062998 on Oct. 2, 2013, now abandoned.

(Continued)

(51) Int. Cl.
*A61B 17/221* (2006.01)
*A61F 2/01* (2006.01)
(Continued)

(52) U.S. Cl.
CPC .. *A61B 17/221* (2013.01); *A61B 2017/00862* (2013.01); *A61B 2017/00867* (2013.01);
(Continued)

(58) Field of Classification Search
CPC ............ A61B 17/221; A61B 17/22031; A61B 17/12168; A61B 17/12172;
(Continued)

(56) References Cited

U.S. PATENT DOCUMENTS 4,706,671 A 11/1987 Weinrib
5,885,258 A 3/1999 Sachdeva et al.
(Continued)

FOREIGN PATENT DOCUMENTS

WO 0222028 3/2002
WO 201307277 A2 5/2013
WO 2014055609 A1 4/2014

OTHER PUBLICATIONS

Extended European Search Report, Application No. 19162401.4, dated Jul. 2, 2019.
(Continued)

*Primary Examiner* — Katherine H Schwiker
(74) *Attorney, Agent, or Firm* — MacMillan, Sobanski & Todd, LLC

(57) ABSTRACT

A minimally invasive blood clot capturing invention made of nitinol. The nitinol is shaped into a plurality of fingers to form a frame for a basket and funnel to capture and remove blood clots. The basket and funnel being delivered to the blood clot by a catheter. The basket and funnel are capable of being collapsed within a catheter, capable of being deployed into a blood vessel, and capable of being retracted into the catheter for removal from the blood vessel.

14 Claims, 21 Drawing Sheets

Related U.S. Application Data

(60) Provisional application No. 61/709,202, filed on Oct. 3, 2012.

(51) Int. Cl.
    *A61B 17/00* (2006.01)
    *A61B 17/22* (2006.01)

(52) U.S. Cl.
    CPC .............. *A61B 2017/2212* (2013.01); *A61B 2017/2215* (2013.01); *A61B 2017/2217* (2013.01); *A61B 2017/22038* (2013.01); *A61B 2017/22079* (2013.01); *A61F 2002/018* (2013.01); *A61F 2230/0067* (2013.01); *A61F 2230/0091* (2013.01); *A61F 2250/0039* (2013.01)

(58) Field of Classification Search
    CPC .... A61B 2017/2215; A61B 2017/2217; A61B 2017/2212; A61B 2017/22031; A61B 2017/22035; A61B 2017/22081; A61B 2017/22038; A61B 17/22032; A61B 17/22034; A61F 2/01; A61F 2/013; A61F 2002/015; A61F 2002/016; A61F 2002/018; A61F 2/0103–0108; A61F 2/012; A61F 2/014
    USPC .......................................................... 606/200
    See application file for complete search history.

(56) References Cited

U.S. PATENT DOCUMENTS

| | | | |
|---|---|---|---|
| 6,146,404 A | 11/2000 | Kim et al. | |
| 6,203,561 B1 | 3/2001 | Ramee et al. | |
| 6,383,205 B1 | 5/2002 | Samson et al. | |
| 6,605,102 B1 | 8/2003 | Mazzocchi et al. | |
| 7,306,618 B2 | 12/2007 | Demond et al. | |
| 8,025,668 B2 | 9/2011 | McCartney | |
| 8,784,434 B2 | 7/2014 | Rosenbluth et al. | |
| 8,968,330 B2 | 3/2015 | Rosenbluth et al. | |
| 9,259,237 B2 | 2/2016 | Quick et al. | |
| 9,408,620 B2 | 8/2016 | Rosenbluth | |
| 9,526,864 B2 | 12/2016 | Quick | |
| 9,526,865 B2 | 12/2016 | Quick | |
| 2002/0123765 A1* | 9/2002 | Sepetka | A61B 17/22031 606/192 |
| 2003/0153943 A1 | 8/2003 | Michael et al. | |
| 2004/0073243 A1 | 4/2004 | Sepetka et al. | |
| 2004/0133232 A1 | 7/2004 | Rosenbluth et al. | |
| 2005/0119668 A1 | 6/2005 | Teague et al. | |
| 2007/0112371 A1* | 5/2007 | Cangialosi | A61F 2/013 606/200 |
| 2007/0167974 A1 | 7/2007 | Cully et al. | |
| 2007/0208367 A1* | 9/2007 | Fiorella | A61B 17/320725 606/198 |
| 2008/0269774 A1 | 10/2008 | Garcia et al. | |
| 2008/0312681 A1 | 12/2008 | Ansel et al. | |
| 2009/0299393 A1 | 12/2009 | Martin et al. | |
| 2010/0268265 A1 | 10/2010 | Krolik et al. | |
| 2011/0152920 A1* | 6/2011 | Eckhouse | A61B 17/221 606/200 |
| 2011/0202088 A1 | 8/2011 | Eckhouse et al. | |
| 2011/0213403 A1* | 9/2011 | Aboytes | A61M 29/02 606/194 |
| 2014/0005714 A1 | 1/2014 | Quick et al. | |
| 2014/0303667 A1 | 10/2014 | Cox et al. | |
| 2017/0071614 A1 | 3/2017 | Vale et al. | |
| 2017/0119408 A1 | 5/2017 | Ma | |
| 2019/0269424 A1* | 9/2019 | Morsi | A61B 17/221 |

OTHER PUBLICATIONS

Notification of Transmittal of the International Search Report and the Written Opinion of the International Searching Authority, or the Declaration dated Feb. 21, 2014.

The extended European search report is enclosed. dated Aug. 12, 2016.

\* cited by examiner

Front View

Side View

Top (Section A-A)

Front View

Side View

Top (Section A-A)

MINIMALLY INVASIVE THROMBECTOMY

CROSS REFERENCE TO RELATED APPLICATIONS

This is a continuation in part of U.S. application Ser. No. 14/433,278 filed on Apr. 2, 2015. This application also claims the benefit of U.S. provisional patent application Ser. No. 61/709,202 filed Oct. 3, 2012 and PC17US13/62998 filed on Oct. 2, 2013.

STATEMENT REGARDING FEDERALLY SPONSORED RESEARCH

The invention was not made with any government support and the government has no rights in the invention.

BACKGROUND OF THE INVENTION

This invention relates to a minimally invasive thrombectomy device for the removal of thrombi (clots) located in blood vessels at different anatomical locations, particularly for pulmonary arteries in the lung.

Many vascular system problems stem from insufficient blood flow. One of the main causes is a blockage within veins known as a blood clot, or thrombus. This can occur after trauma, surgery, or other phenomenological reasons. The ultimate goal of any percutaneous modality to treat these conditions of the arterial or venous system is to remove the blockage or restore patency, quickly, safely, and cost effectively. This can be achieved by thrombus dissolution, fragmentation, thrombus aspiration, en bloc removal, or a combination of these methods.

Pulmonary embolism (PE) is a fatal condition that occurs when clots move to pulmonary arteries causing blockage of the arteries leading to respiratory failure, right ventricular failure, and death Pulmonary embolism is the third most common cause of death for hospitalized patients.

Intravenous and oral anticoagulation are the most common modalities for treating PE. For patients with more severe PE, such as massive (5% of patients) and submassive PE (40% of patients), these medications may not resolve the thrombus burden in a rapid enough fashion, and additional therapies are needed to remove the clot and restore the blood flow Other treatments that are used less frequently in open heart surgery for manual removal of the clot (surgical embolectomy), thrombolytic medications, and catheter-directed treatments. Each of these carries substantial risks for patient outcomes, particularly open-heart surgery, while thrombolytic medications can cause bleeding throughout the body and in the brain, and catheter-directed treatments require long treatment periods, and large catheters. Percutaneous thrombectomy of thrombus is a new approach that has been recently introduced to mechanically remove an embolus from blood vessels. Thrombectomy devices involve the use of catheters to minimally-invasively reach and remove a thrombus. Percutaneous thrombectomy is the removal of thrombus using non-surgical methods. Percutaneous thrombectomy can be used to remove thrombus from arteries, veins and vascular grafts and can be used alone, as a primary procedure, or in combination with transcatheter thrombolysis or angioplasty and stenting.

Catheter directed thrombectomy and thrombolysis is less traumatic and avoids the morbidity and mortality associated with conventional surgical techniques. It also has the advantage of providing diagnostic information about associated vascular diseases and to treat coexisting lesions. As a result, there has been a push for the use of percutaneous mechanical thrombectomy (PMT) devices. These devices offer a key advantage over surgical thrombectomy or thrombolysis. The concept of the mechanical thrombectomy is attractive, however, developing a miniature device that can quickly and atraumatically restore patency to a vessel without creating some degree of distal embolization is a goal that still eludes the medical community.

An invention based on the use of super-elastic alloy nitinol has been developed that offers several advantages over PMT devices currently on the market. This invention provides a higher degree of authority and maneuverability for capturing and removing blood clots. A major issue with existing PMT inventions is shearing off of smaller particles (embolic particles) during the process of dot removal. The thrombi of PE are often larger in diameter than the catheters used for PMT, and there is often fragmentation and further embolization of thrombus during the removal process. Distal Embolization occurs when either the dot itself or the embolic particles travel downstream and occlude another vessel in the body. Distal embolization is known to lead to fatal complications in the treatment of pulmonary embolism, when the secondary clots move to pulmonary arteries in the lungs, or a stroke, when the secondary clots occlude the vessels in the brain. In the U.S., the number of fatalities due to pulmonary embolism alone is known to be approximately 200,000 per year. The invention is capable of removing a thrombus while minimizing distal embolization and therefore reducing the risk of secondary clot formation and the related complications and fatalities.

This invention is capable of removing different sizes en bolus safer, quicker and more efficiently than currently available procedures.

SUMMARY OF THE INVENTION

The present invention generally refers to a minimally invasive blood clot capturing device made of nitinol. The invention is deployed by a catheter that is introduced into the body using the modified Seldinger technique. The catheter is driven to a blood clot and the operator deploys the invention out of the catheter. The invention evacuates thrombus without shearing the blood clot into smaller pieces. Current PMT devices that operate to pull-back and capture a thrombus have no way of guiding a blood clot into an exiting catheter without shearing pieces of blood clot which can escape downstream and create, in some instances, problems that are worse than the initial obstruction. Due to practical limitations regarding catheter sizes that are appropriate for accessing human vessels, in most cases, the blood clot has a diameter that is larger than that of the aspiration catheter. This invention specially addresses this critical design challenge by using a nitinol proximal basket to encircle the thrombus during the aspiration and removal phase. With the introduction of this invention, loss of emboli is drastically reduced most situations.

Accordingly, an object of subject invention is to provide a method and system that completely removes thrombus in blood vessels safely and efficiently.

Still another object of the present invention is to minimally-invasively treat patients with pulmonary embolism by completely and quickly removing different sizes and shapes of thrombus from the pulmonary arteries without causing any trauma to the blood vessels. Various aspects of this invention will become apparent to those skilled in the art from the following detailed description of the preferred embodiments, when read in light of the accompanying drawings.

DETAILED DESCRIPTION

Figure 1:
FIG. 1 is a perspective view of the laser spiral cut nitinol tube prior to shape setting.

Specific embodiments of the invention will now be described with reference to the accompanying drawings. The invention provides a novel method and system to conduct a thrombectomy using is combination of trapping, snaring and aspiration mechanisms to remove different sizes of thrombus from a blood vessel, particularly pulmonary arteries treating patients with pulmonary embolism. Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Before the instant invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments and is not intended to be limiting. instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

Throughout the entire specification including the claims, the word "comprise" and variations of the word, such as "comprising" and "comprises," as well as "have," having," "includes," "include," and "including," and variations thereof, means that the named steps, elements or materials to which it refers are essential, but other steps elements, or materials may be added and still form a construct with the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps.

The term "nitinol" herein is used to describe a metal alloy comprised of nickel and titanium where the two elements are present in approximately equiatomic percentages. The term superelastic herein is used to describe a property of nitinol of a certain chemical composition in which a deformation is recovered without it being necessary to heat the nitinol alloy.

Thrombus is used to describe a blood clot, the final product of a blood coagulation step in hemostasis. As such the terms thrombus and clots are used interchangeably.

Figure 2:
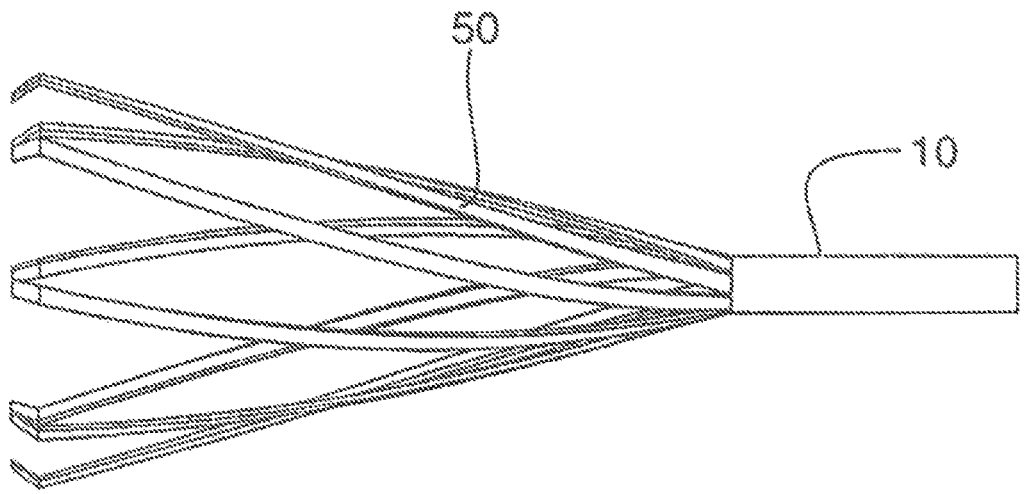
FIG. 2 is a perspective view of the laser spiral cut nitinol tube after shape setting.
Figure 3:
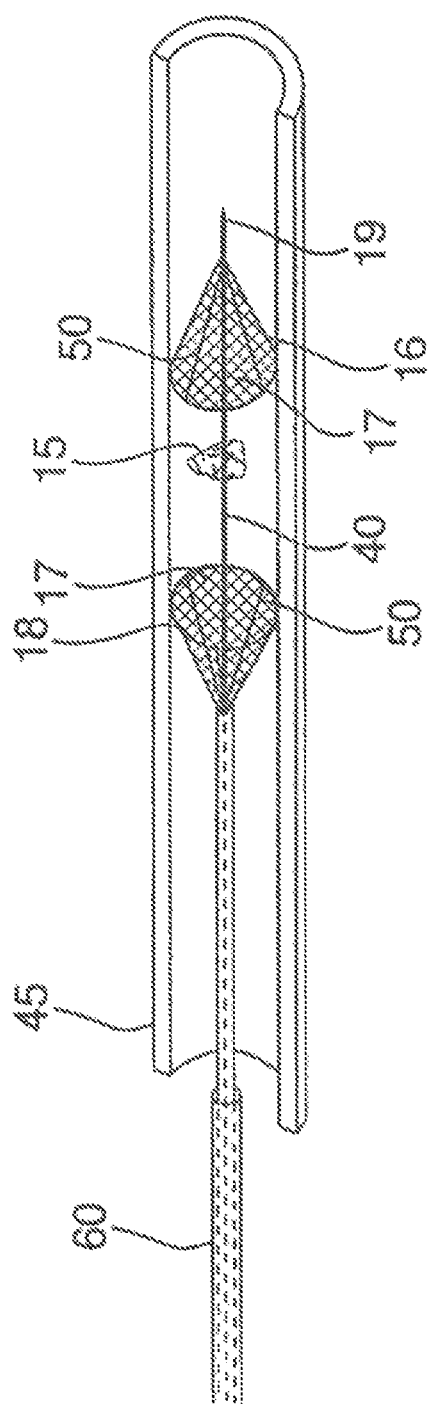
FIG. 3 is a perspective view of the invention, showing both elements of the invention, the basket and funnel, deployed to capture a blood clot between the two elements.
Figure 4:
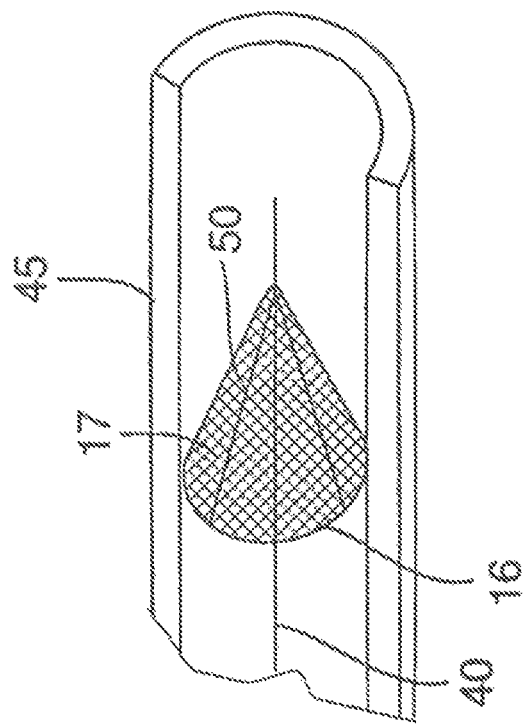
FIG. 4 is an expanded perspective view of the collection basket.
Figure 5:
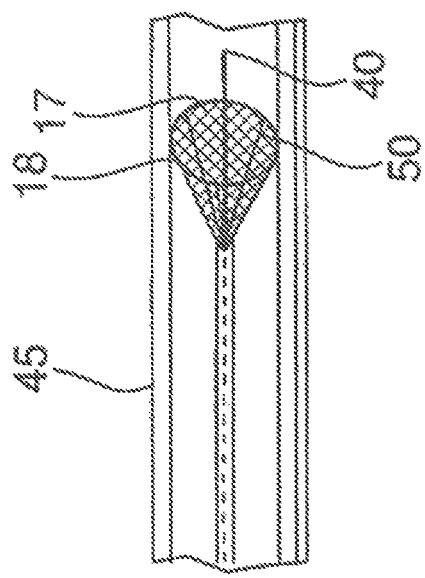
FIG. 5 is an expanded perspective view of the funnel.
Figure 6:
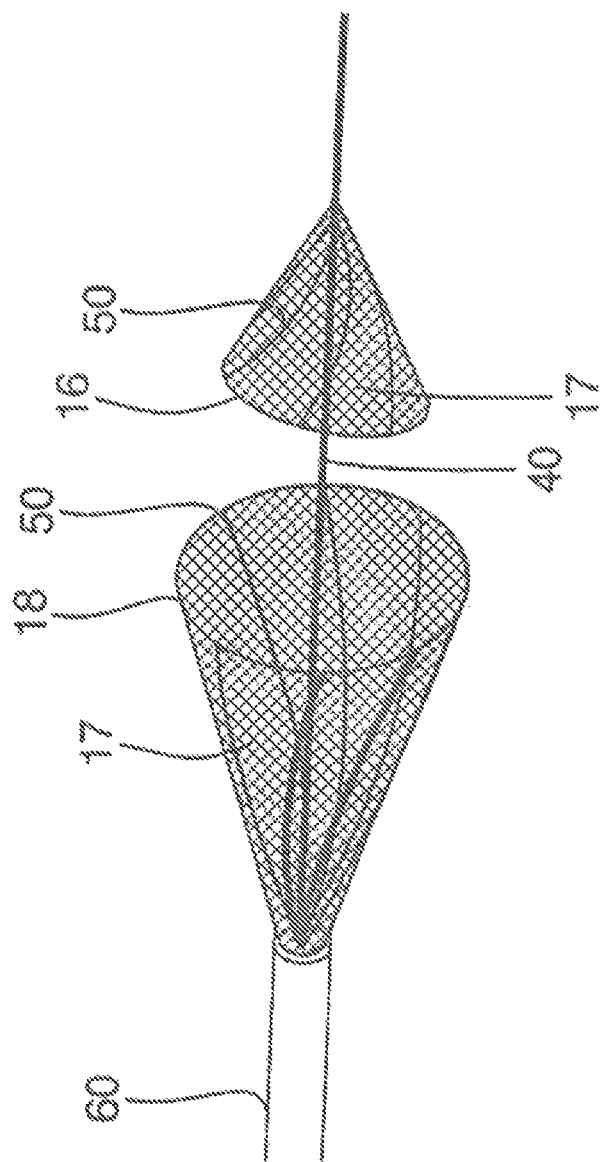
FIG. 6 is a perspective view of the invention.
Figure 7:
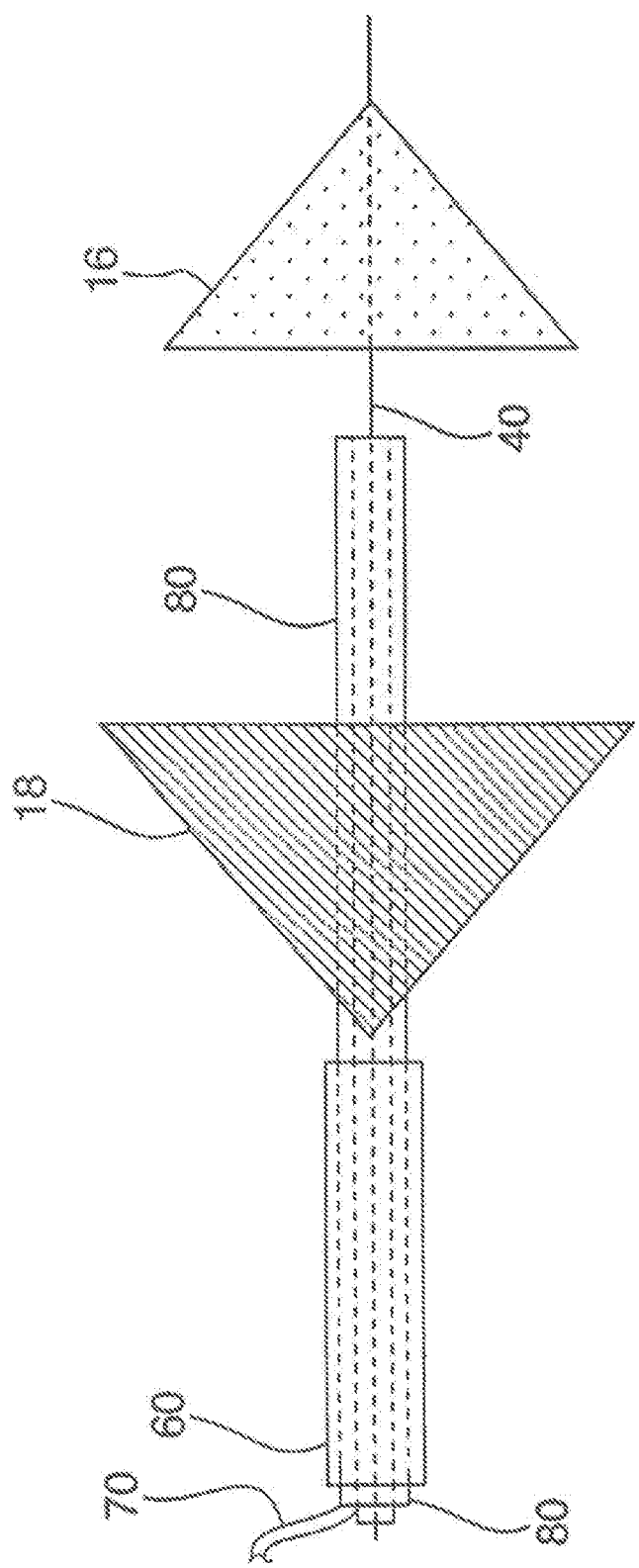
FIG. 7 is a schematic view of FIG. 3.
Figure 11:
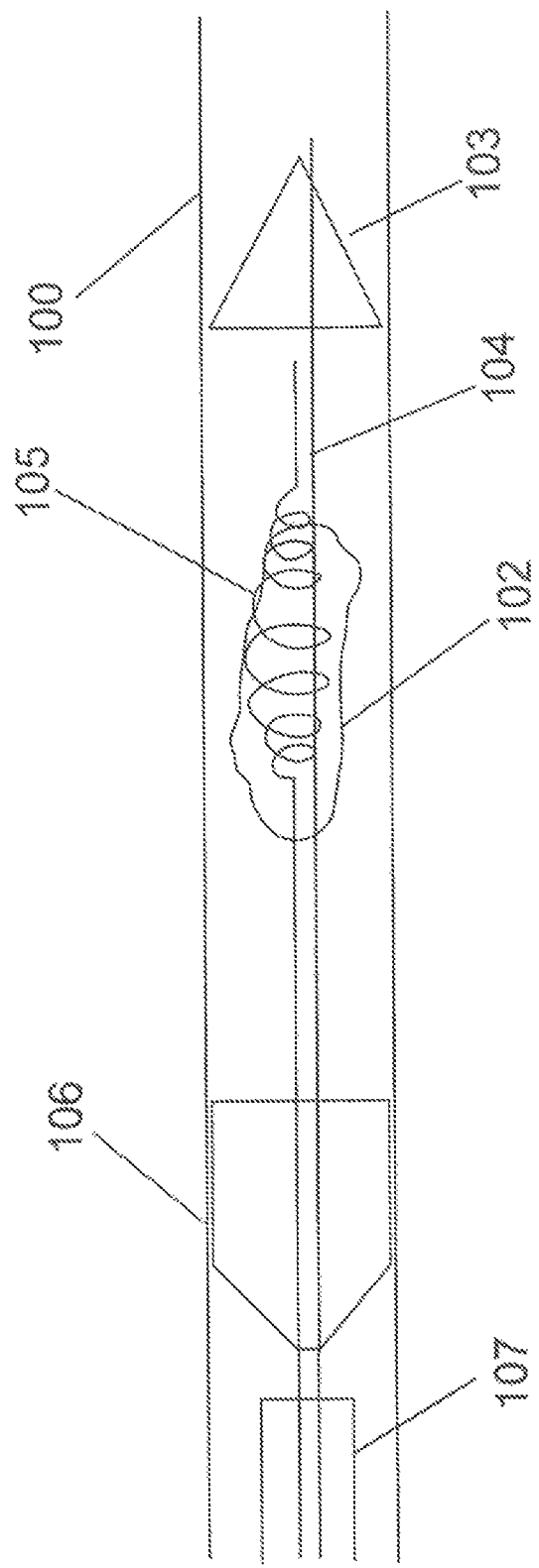
FIG. 11 is a side elevational view of the invention.
Figure 12:
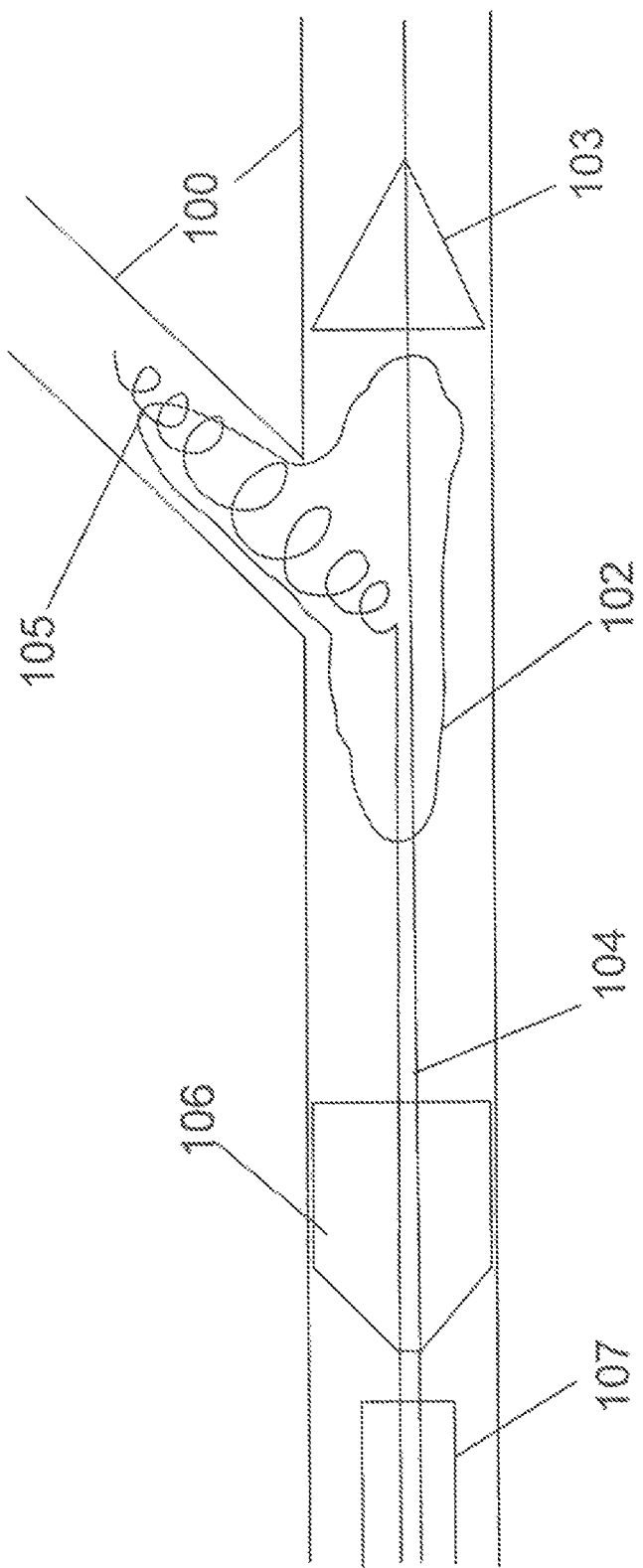
FIG. 12 is a side elevational view of an alternative structure of the device.

Referring now to FIGS. 1-3 the invention is a percutaneous catheter-based device that uses a pair of superelastic nitinol capturing elements to aid in the collection of a thrombus and minimize distal embolization. The invention, being made of nitinol and once it is unrestricted by the catheter, changes shape to create a basket 16. The invention has two components of a superelastic nitinol tube 10 that have been partially laser cut longitudinally and shape set to create a cone of superelastic fingers. FIG. 1 shows the nitinol tube 10 as cut by the laser cutting process prior to shape setting. This same cutting process, illustrated in FIG. 1, is used to create both, the basket 18 and a funnel 18. FIG. 2 illustrates how a plurality of fingers 50 are shape set into the expanded position. FIGS. 11-12 illustrate the preferred embodiment wherein the plurality of fingers 50 of the basket 16 and the funnel 18 can be spiraled or have a helix shape to maximize contact the nitinol fingers of the basket 16 and funnel 18. To further ensure contact of the nitinol fingers, the plurality of fingers 50 are spiraled in opposite directions. The basket 16 and the funnel 18 are covered in a blood permeable membrane 17 such as expanded Polytetrafluoroethylene (ePTFE), BioWeb, or other membranes, capable of allowing blood flow while capturing blood clots, or may omit such a membrane and use a nitinol mesh with designed pore sizes. To reduce the risk of puncturing a blood vessel 45, the plurality of fingers 50 may be rounded, further, the tips of the fingers 50 may be flattened and/or curved inward 51 as illustrated in FIG. 2. The basket 16 and the funnel 18 may be made from superelastic nitinol or other metal alloy exhibiting superelastic properties. The spiral orientation of the plurality of fingers 50 also reduces the risk of tearing the membrane 17.

In the preferred embodiment the invention is deployed using an outer catheter 60 and an inner catheter 80. The invention is deployed by constricting the basket 16 within the inner catheter 80 and by constricting the tunnel 18 with the outer catheter 60. The outer catheter is directed to the blood clot 15. The outer catheter is partially retracted to deploy and expand the funnel 18. The inner catheter 80 and the basket 16 are guided to the distal end of the blood clot 15 and the inner catheter is fully removed to deploy and expand the basket 16. A guide wire 40 is used to draw the basket 18 to the blood clot 15. Pulling the basket 16 through the blood clot 15 will cause the blood clot to lodge into the basket 16. A guide wire 40 is withdrawn to guide the basket 16 into the funnel 18. The funnel 18 and the basket 16 are drawn into the outer catheter 60 collapsing the funnel 18 onto the basket 16 and thus collapsing the basket inside the funnel and trapping the blood clot within. In other embodiments additional catheters 70 may be used to provide suction, deploy multiple baskets, or other devises to dislodge the blood clot 15.

In the preferred embodiment the funnel 18 and the basket 16 are used in conjunction, however it is envisioned that the funnel or basket could be deployed individually, or in combination with other PMT devices.

The basket 16 may have a probe 19 located on the end to assist in moving the basket to the distal end of the blood clot 15. The catheter can be withdrawn leaving behind and deploying the basket 16. Once the catheter is withdrawn the plurality of fingers 30 of the basket 16 expand to the predetermined shape. A similar process takes place proximal to the blood clot 15. The funnel 18 is advanced out of a constraining catheter where it expands to nearly the diameter of the vessel lumen. The superelastic property of nitinol assists in expanding the nitinol material that forms the basket 16 and the funnel 18. The guide wire 40 extends to the basket 18 and through the funnel 15. The guide wire 40 is advanced in a direction towards the funnel moving the basket towards the funnel. This movement brings the basket 16 into contact with the blood clot 15 whereby the basket can remove the blood clot from the blood vessel by trapping the blood clot within the basket 16.

Figure 9:
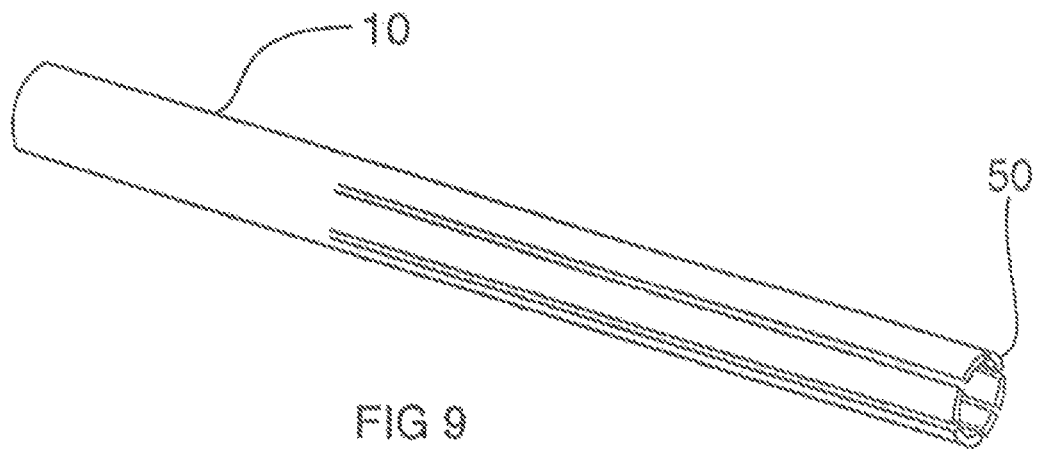
FIG. 9 is a perspective view of the laser straight cut nitinol tube prior to shape setting.
Figure 10:
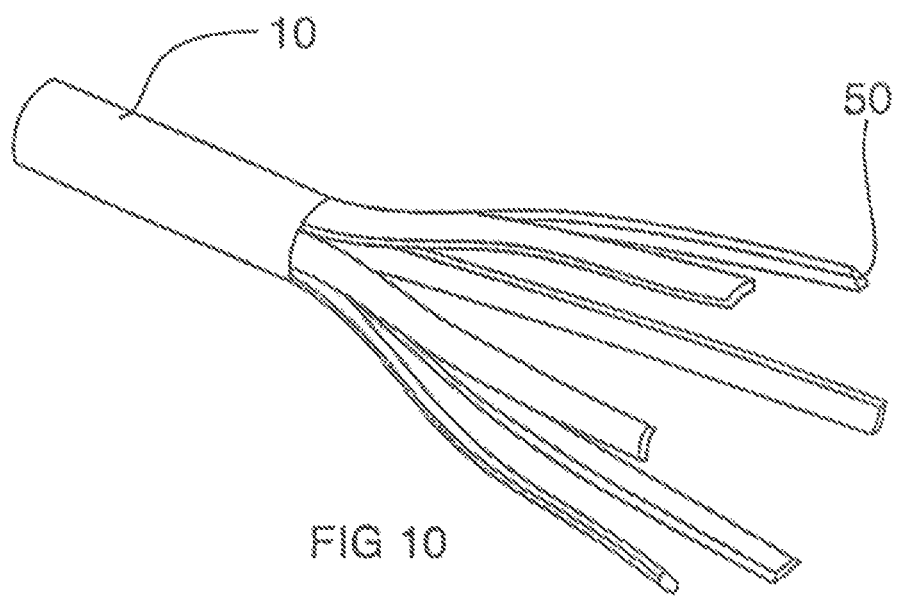
FIG. 10 is a perspective view of the laser straight cut nitinol tube after shape setting.

FIGS. 9 and 10 illustrate different embodiments of the invention wherein the plurality of fingers 50, are straight and not spiral shaped. Other shapes may be used for the plurality of fingers 50.

In some applications it may be preferable to have control wires that extend through the funnel 18 and engage the outer periphery of the basket 16. The control wires can be moved individually or as a group to position the outer periphery in a position adjacent to the clot 15. The control wires can help to position the basket 16 in the best position to capture the clot. In some instances, the control wires can be used to assist the basket in removing the clot from the wall of the blood vessel.

A source of suction may be directed to the portion of the blood vessel that is located between the basket 16 and the funnel 18. The suction is used to remove fluid and particles from the blood vessel during the time that the blood clot 16 is being removed from the blood vessel. The basket is withdrawn capturing the blood clot 15. The basket 16 can be withdrawn and nested in the funnel 18. Aspiration of the blood clot 15 can be performed if desired by applying manual suction with a syringe on the funnel 18 catheter. Once nested, the two nitinol components of the invention collapse by withdrawing the funnel 18 catheter within the outer catheter 60 taking the basket 16 and clot with it.

In some applications the funnel 18 and the basket 16 can be positioned using separate catheters or the same catheter. Suction can be provided through a catheter that positions the basket 16, the funnel 18, or a separate catheter 70 may be used to provide the suction. It should also be appreciated that either the basket 15 or the funnel 18 may be deployed or opened first in the blood vessel depending on how the blood clot 15 is to be removed.

The basket 16 and the funnel 18 are made of a material which is opaque for medical imaging equipment to allow for monitoring of the placement of the basket and funnel relative to the blood clot 15. In some procedures it may be desirable to use a balloon on the distal or proximal side of the blood clot. The balloon can be used to stop or control the flow of blood through the vessel during the Clot removal procedure.

Two components of superelastic nitinol tube 10 have been partially laser cut longitudinally and shape set to create a cone of superelastic lingers FIG. 2. A Techne FB-08 fluidized alumina furnace may be used for the shape setting. Alternatively, the baskets may be formed from woven nitinol wires and then heat-set for the desired shapes.

Different embodiments of the invention can include varying diameters of nitinol tubing 10 as well as varying diameter of the final shape set size of collection basket 16 and/or funnel 18. Since the human circulatory system includes vessels of many different sizes, the invention may be scalable to be used in various locations of the body.

EXAMPLE

A simulated circulatory system was built to test me present invention along with a commercially available PMT device. The setup features a reservoir physiologic saline solution pumped through a system of tubing using a peristaltic pump. The network of tubes splits into a testing branch and a bypass branch. The testing branch has an acrylic chamber that is tapered to simulate an arterial or venous stenosis. This section of the testing environment was designed such that an artificial clot would become stuck in this section and the inventions could be used as they would be clinically. A three-stage cascading filtration system was installed downstream from the testing chamber to capture any embolic particles.

A peristaltic pump (Ismatec MCP Standard) was programmed to simulate the pulsate flow from the heart. The maximum pressure was approximately 120 mmHg, the minimum pressure was approximately 80 mmHg, and the maximum velocity was about.

A 10 mL sample of fresh blood was transferred to an intermediate 15 mL test tube. A pipette was then used to transfer 9 mL of blood to twelve, 2 mL test tubes creating twelve samples of 750 μL of blood. These twelve samples were allowed to incubate at 22° C. for 24 hours. This procedure was done twice: once to create twelve clots to test the present invention and once to create twelve clots to test a commercially available PMT device.

A DiverCE Rapid Exchange Clot Extraction Catheter (INVATEC S.p.A. Roncadelle (Bs) Italy) was chosen as the commercially available PMT to test under the same conditions as the present invention. The DiverCE is an aspiration invention that uses manual suction with a syringe to evacuate a clot. There are two version of the DiverCE, one for "organized thrombus" and one for "fresh thrombus". The version for fresh thrombus was used for this test.

Blood Clots were created and placed in the system. The system was then sealed, and the pump was activated. The present invention was introduced via percutaneous puncture of the laboratory tubing. The invention was withdrawn and the blood clot 15 was captured and removed. This procedure was repeated twelve times. The DiverCE catheter was operated as outlined by the manufacturer's instructions for use in each of the twelve trials.

Data was collected using the three-stage cascading filtration system. Stainless steel filters were used to capture any embolic material. Filter #1 closest to the clot had a pore opening size of 102 μm. Filter #2, the middle filter, had a pore opening size of 25 μm. The last filter, Filter #3, had a pore size of 5 μm. A set of three filters (#1, #2, and #3) were weighed prior to performing a capturing trial with either the present in or the DiverCE The filters were installed into the designed flanges and the test was conducted. After the capturing procedure Was completed and the pump deactivated, the tubing was evacuated of saline via a laboratory vacuum such that ail possible particles would be captured by the filtration system. The filters were removed and allowed to dry for 24 hours. The filters were reweighed, and any mass gain was recorded. New filters were used for each trial.

Figure 8:
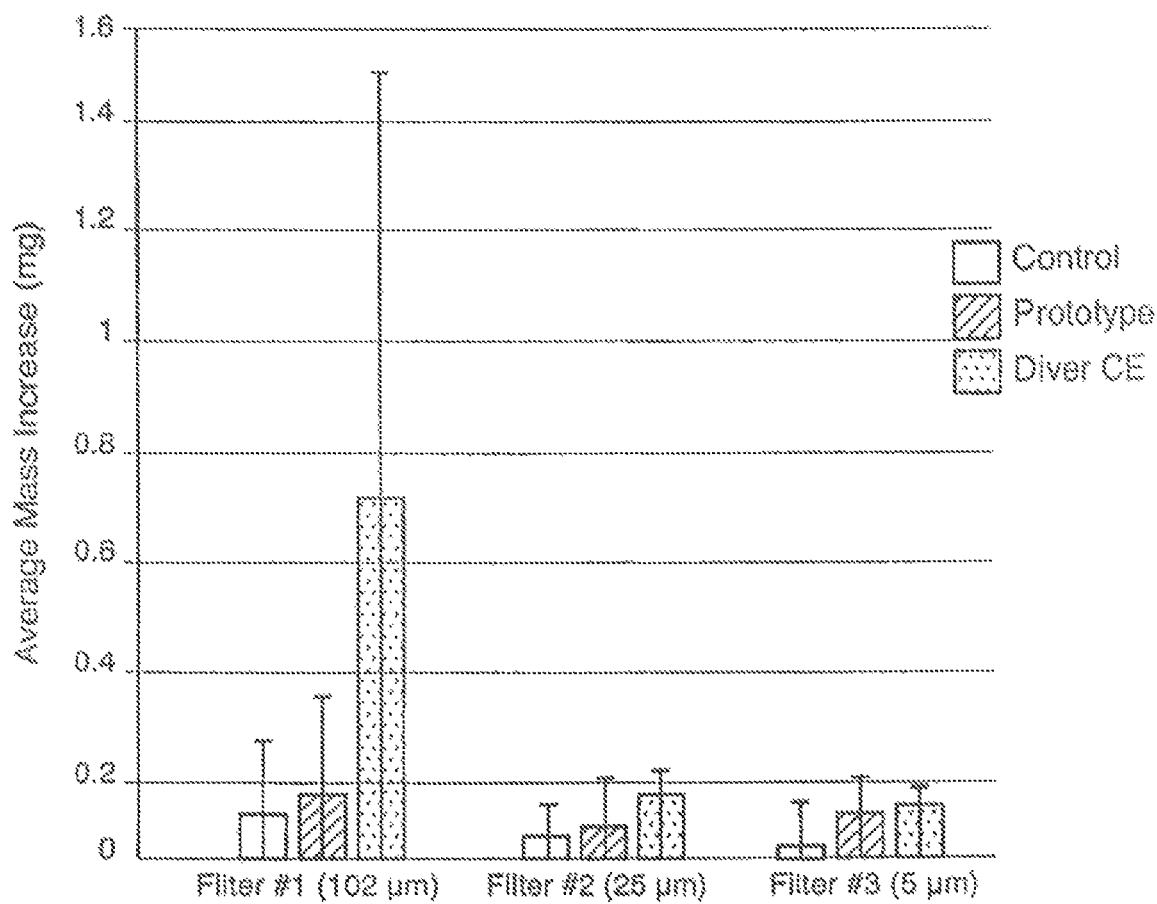
FIG. 8 is a graph showing the results of testing, error bars show ± standard deviation.

A control study was also conducted. Saline solution was allowed to flow over a series of three filters (#1, #2, and #3) for a period of twenty seconds. Filters were weighed nor to saline flow and after 24 hours of drying time. Any mass increase was recorded, and results are shown in FIG. 8. As illustrated by FIG. 8, the present invention outperformed the commercially available DiverCE at each stage and drastically reduced embolic particles.

Referring to FIGS. 11-31, additional features of the invention are shown. The basic operation of the invention is essentially the same as previously described. The apparatus comprises of three primary devices made of superelastic nitinol that can be positioned inside a blood vessel 1: (i) an expandable basket 103 connected to a guide wire 104 positioned on the distal side of the thrombus 102, (ii) a wire 101 with a spiral counter-rotating conical tip 105, and (iii) an expandable funnel 106 positioned on the proximal side of the thrombus 102.

The wire 100 with a spiral counter-rotating conical tip 105 independent of the expandable basket 103 and guide wire 104 system which gives the physician or user the freedom to remove thrombus in different branches simultaneously such as in the case of saddle pulmonary embolism (saddle thrombus 108), see FIG. 12.

The wire 101 with a spiral counter-rotating conical tip 105, alternatively, may be connected to the expandable basket 103, in which case, the wire and basket can work as a single device. This eliminates the need for wire 104 which reduces the complexity of the procedure especially when the apparatus is used for removing a normal thrombus located in one blood vessel, see FIG. 13. In some applications, the wire 101 may not be necessary and the wire 104 will be used separately with basket 103.

The wire 101 with a spiral counter-rotating conical tip 105 and the expandable basket 103 independent from each other or as one device, are disposed and pulled towards the distal side of thrombus 102 to capture and move the thrombus into the funnel 106 disposed of a main sheath 107.

The first step for using the invention includes positioning a guidewire at the proximal side of the thrombus 102 or 108. One example of a guide wire is a flexible 0.035" nitinol guidewire. The guidewire is positioned using a common technique called "Seldenger Technique". For instance, the guidewire is positioned in the pulmonary artery by firstly placing it into the femoral vein using percutaneous puncture and then up vena cave and through the right atrium and right ventricle into the pulmonary artery to the location of the thrombus.

Figure 22:
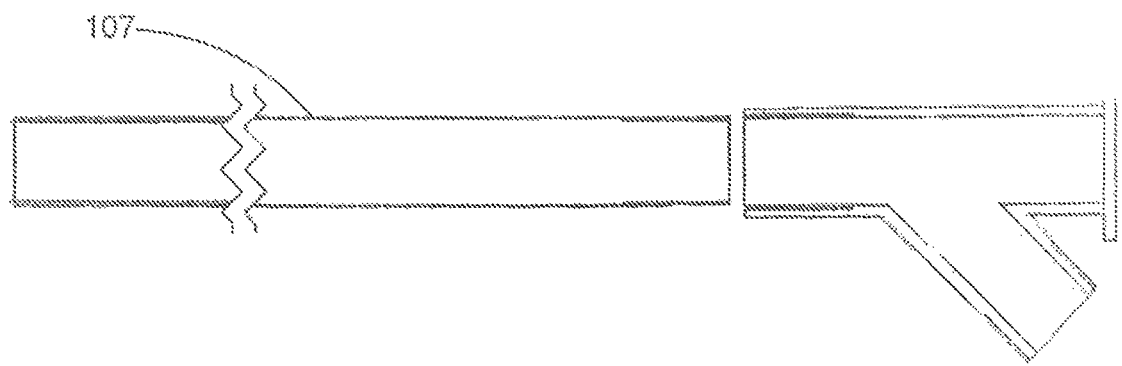
FIG. 22 is a side elevational view of a component of the device.

Using a dilator, the main sheath 107 is guided over the guidewire in place to the proximal side of the thrombus 102 or 108. The end of the main sheath is inside the body at the proximal side of the thrombus, while the beginning of the sheath is outside the body with a hemostatic valve that is used to insert the apparatus into the body. The end of the main sheath stays inside the body during the procedure until the complete removal of the thrombus. The feature of the main sheath 107 are shown in FIG. 22. The sheath shown is an example of a deliver/system that can be used with the clot removal device of the invention.

The funnel 106 is firstly constricted and inserted through the main sheath 101 all the way until the end of the main sheath 107. Once the funnel 106 is outside the main sheath 107 at the proximal side of the thrombus 102 or 108, it expands to a predetermined shape and expands to a diameter at the open end of the funnel that is essentially the diameter of the blood vessel. The funnel 106 been uniquely designed to achieve thrombus capture and retrieval en bloc. The funnel has a conical section 106 and a cylindrical section 109. The conical section has a length from about 15 mm to about 50 mm. The cylindrical section extends from the conical section and forms the opening for the funnel. The opening in the funnel has a diameter from about 10 mm to about 50 mm, the size of the opening is dependent on the size of the vessel where the funnel is deployed. The central problem of percutaneous thrombectomy is that the thrombus is often larger in diameter than the orifice of the sheath used for aspiration. Most often, this results in shearing and fragmentation of thrombus with minimal thrombus capture. The funnel 106 has been designed to specially address this critical challenge. It is designed with an elongated cylindrical extension 109 at the open end of the funnel, of at least 5 mm and up to 100 mm in length with a preferred length from about 20 mm to about 40 mm. The extension designed to be in contact with the inner walls of the blood vessel 101, see FIG. 16. The funnel is enlarged and elongated to entirely encompass the basket 103, wire with spiral counter-rotating conical tip 105, and the thrombus. By encircling the thrombus and then constraining the thrombus during the removal process as the baskets are withdrawn into the outer sheath, the proximal basket is able to contain the thrombus and prevent embolization of thrombus during the removal process. This allows the device to retrieve larger thrombi without any loss of thrombus as the device is retrieved back into the main sheath 107. In addition, the cylindrical extension 109 results in a longer contact surface with the inner walls of the blood vessel 101 which reduces the forces on the blood vessel and possible blood vessel trauma. The cylindrical extension 109 also engages the walls of the blood vessel and acts as a barrier for allowing the thrombus or any portion of the thrombus from moving past the funnel as the thrombus is removed. The funnel 106 is connected to a small cylindrical tube "cuff" 110 to allow for maximum lumen diameter during aspiration, see FIG. 16. The end of the cuff 110 is connected to a stiff metallic mandrel 111 with a handle grip 112 at its end, outside the body, for a better maneuverability and control of the funnel system. The tube cuff 110 is positioned in the main sheath 107 during insertion into the patient.

Figure 13:
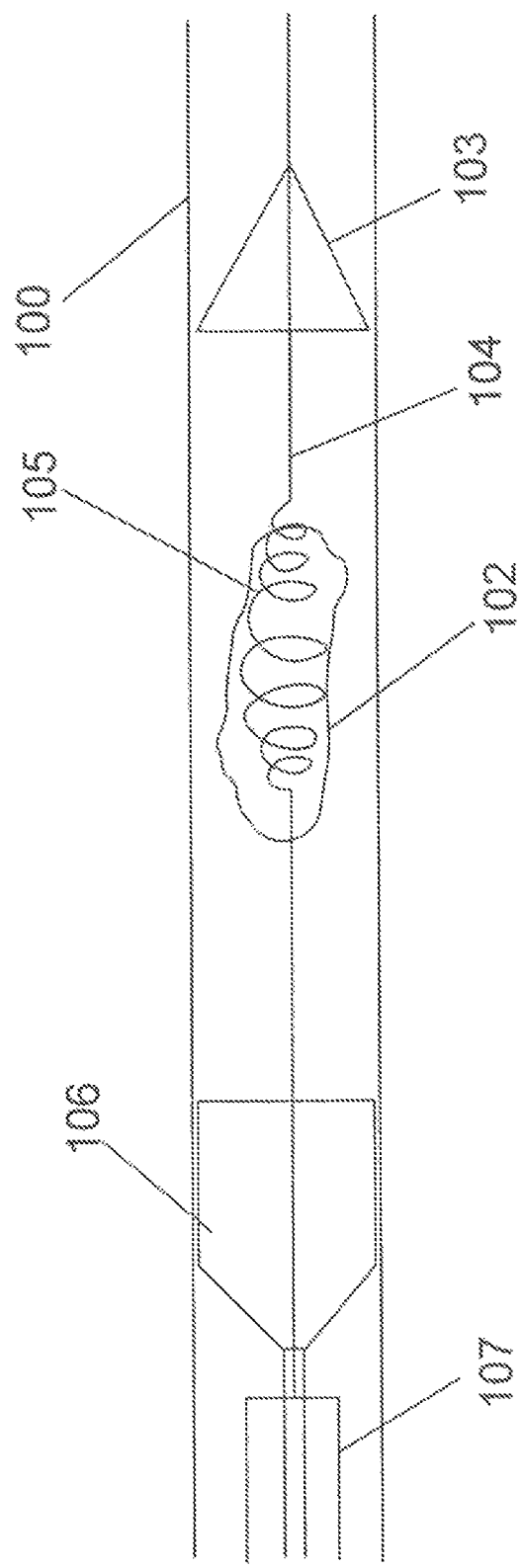
FIG. 13 is a side elevational view.
Figure 14:
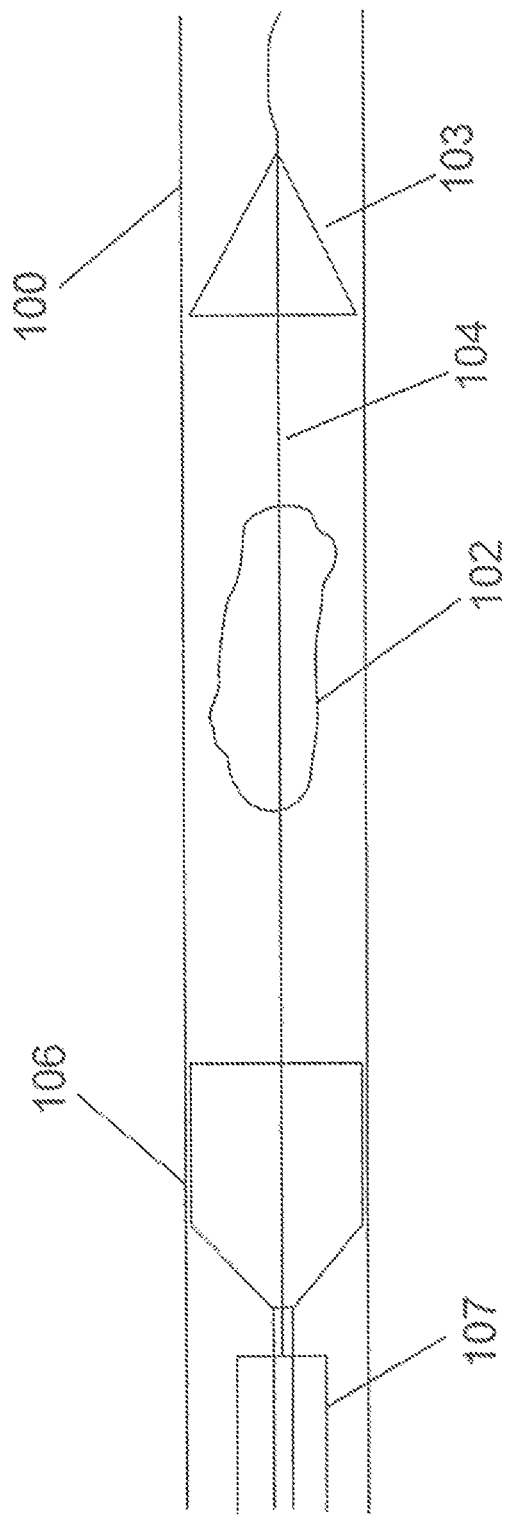
FIG. 14 is a partial side elevational view.
Figure 15:
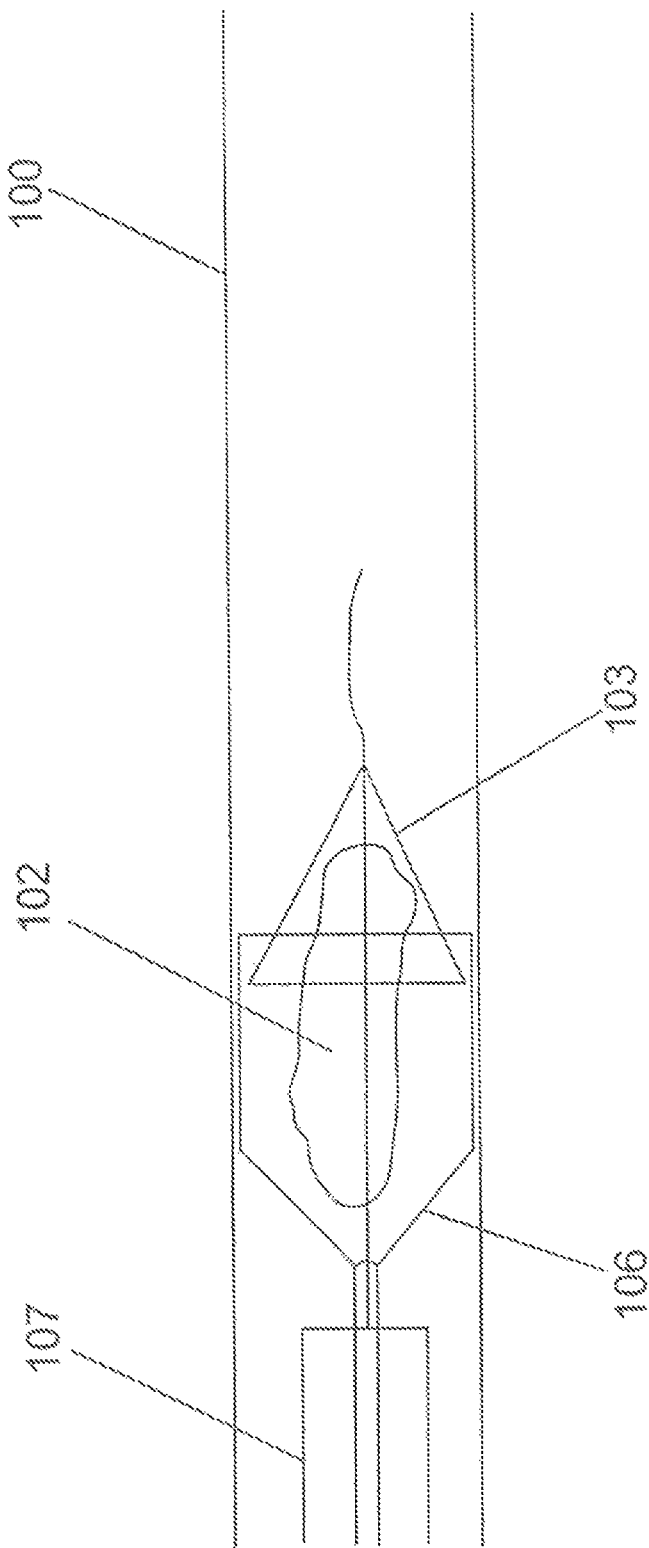
FIG. 15 is a partial side elevational view.
Figure 16:
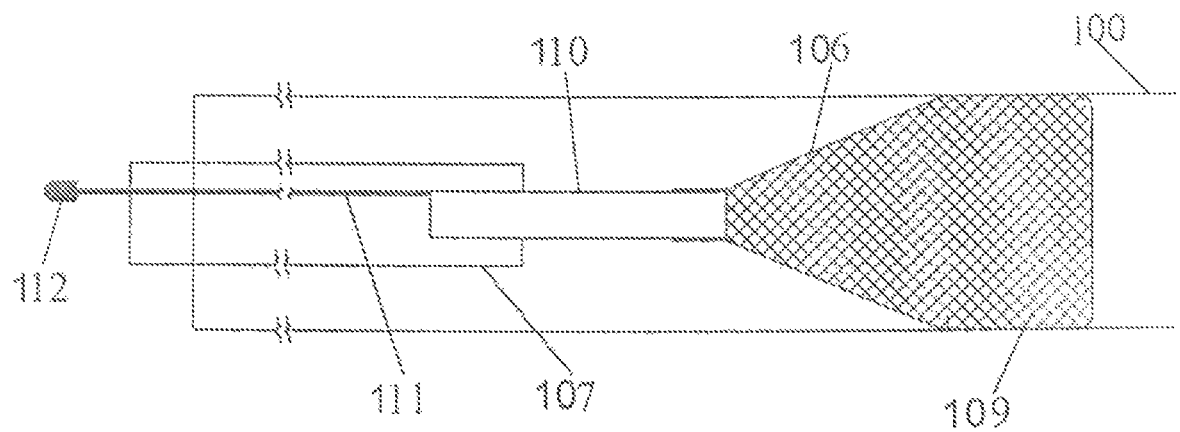
FIG. 16 is a partial side elevational view.
Figure 17:
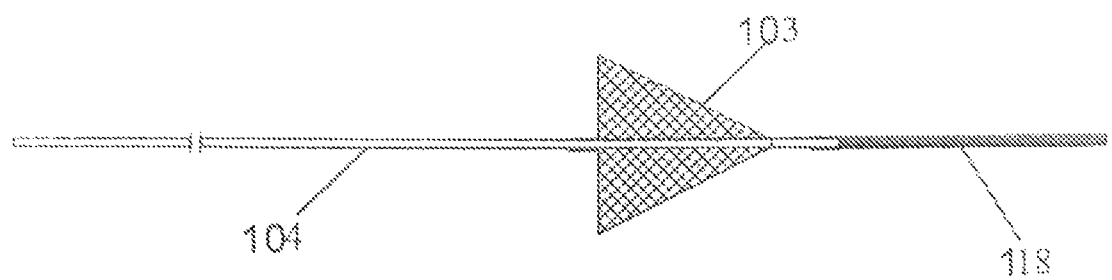
FIG. 17 is a partial side elevational view.
Figure 18:
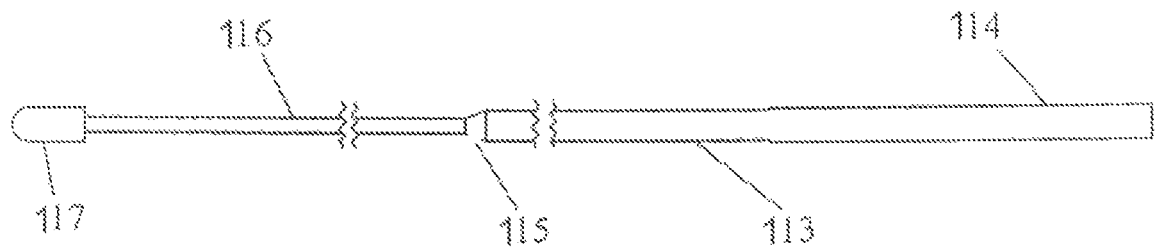
FIG. 18 is a partial side elevational view.
Figure 23:
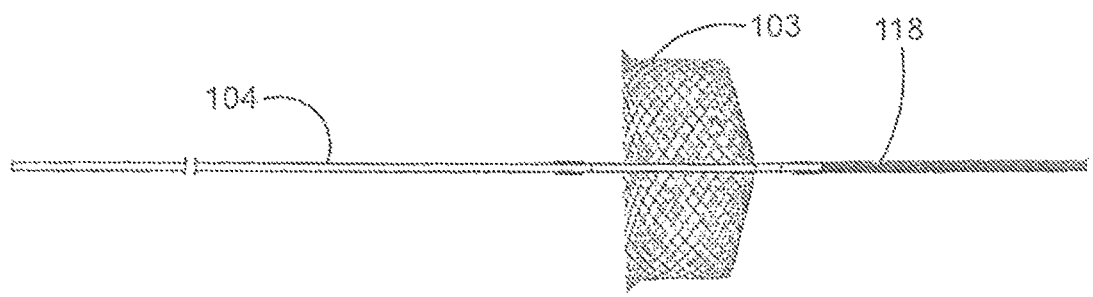
FIG. 23 is a side elevational view of another feature of the device.
Figure 24:
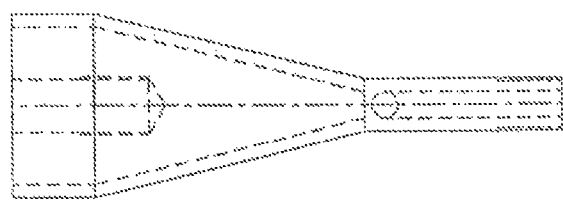
FIG. 24 is a side elevational view of a feature of the invention.
Figure 26:
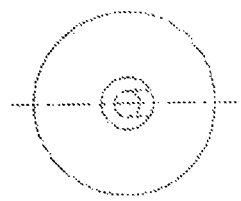
FIG. 26 is an end view of the feature of FIG. 24.
Figure 25:
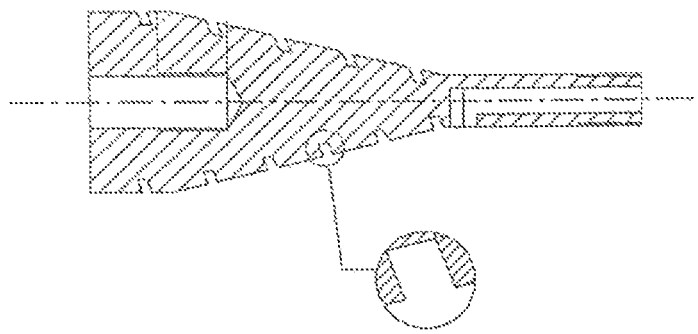
FIG. 25 is a top view of the feature of FIG. 24.
Figure 27:
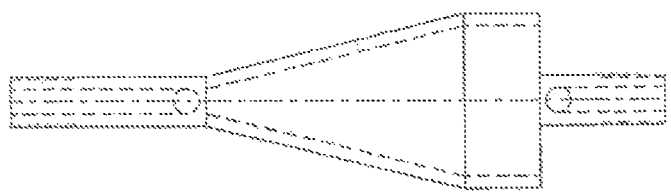
FIG. 27 is a side elevational view of a feature of the invention.
Figure 29:
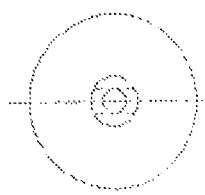
FIG. 29 is an end view of the feature of FIG. 27.
Figure 28:
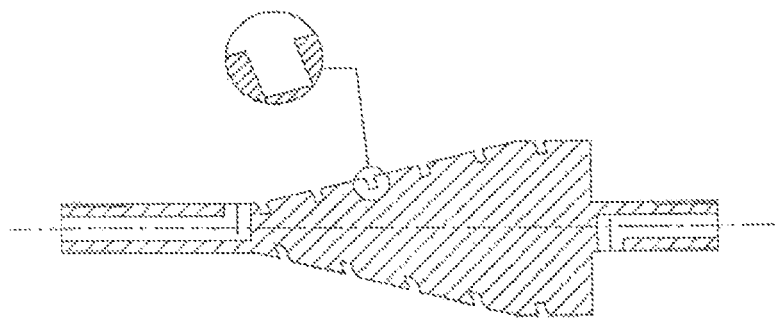
FIG. 28 is a top view of the feature of FIG. 27.

After the funnel 106 is placed through the main sheath 107 at the proximal side of the thrombus 102 or 108, a small delivery catheter 113 constricting the basket 103 is inserted through the main sheath 107, the tube cuff 110 and the funnel 106 past the thrombus. Once the delivery catheter 113 is in location, the basket 103 is then released and deployed to a predetermined shape and diameter by retrieving its constraining delivery catheter 113 while keeping the basket 103 and wire 104 in location. The basket can have a generally conical or cylindrical shape. FIG. 23 shows the cylindrical shape for the basket 103. The length of the basket is from about 5 mm to about 50 mm and the opening of the basket has a diameter from about 10 mm to about 40 mm. the diameter of the opening being dependent on the size of the vessel where the basket is deployed. When the basket 103 has a cylindrical shape, the sidewall of the cylindrical basket will engage or be close to the wall of the blood vessel. The sidewalls of the cylindrical basket can engage the thrombus and assist in removing the thrombus from the blood vessel. FIG. 13 shows that the wire 104 is connected to the basket 103 from its distal end. Both the wire 101 with spiral counter-rotating conical tip 105 and the wire 104 have a soft and flexible distal tip 118 to allow for easy shaping and maneuvering, see FIG. 17. The details of the delivery catheter 113 for basket 106 are shown in FIG. 18. The catheter has an enlarged atraumatic expansion tip 114 to house the constricted basket 103. At the connection between the catheter 113 and a stiff metallic mandrel 116, there is an opening 115 that is used as a "rapid exchange" to allow for a quick delivery and deployment of the basket 103. The end of the mandrel, outside the body, has a handle grip 117 for a better maneuverability and control of the basket delivery catheter.

Figure 19:
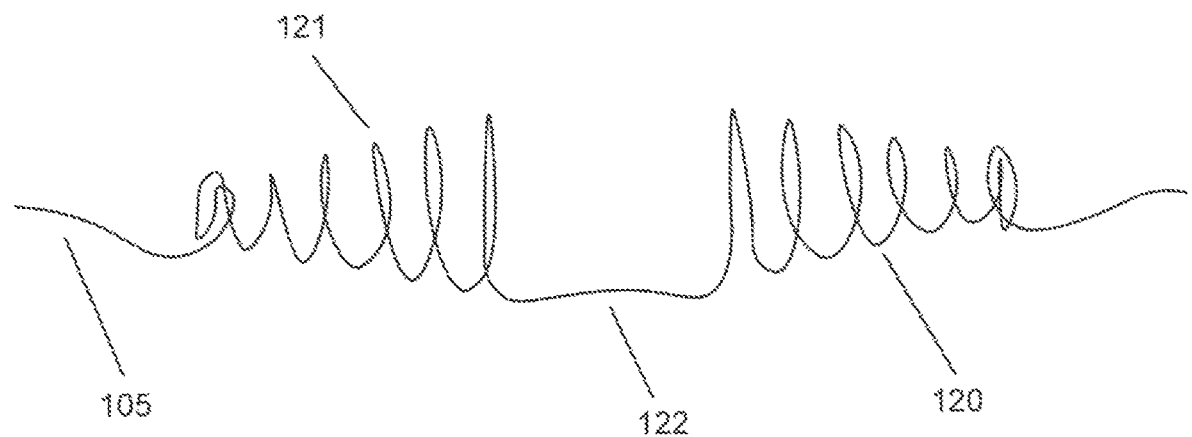
FIG. 19 is a side elevational view of a part of the device.

Another delivery catheter 119 constricting the wire 101 with a spiral counter-rotating conical tip 105 is inserted through the main sheath 107, the tube cuff 110 and the funnel 106 to the location of the thrombus 102 or 108. The wire with a spiral counter-rotating conical tip 105 is then released and deployed by retrieving its constraining delivery catheter 119 while keeping the wire with a spiral counter-rotating conical tip 105 in location in the blood vessel. FIG. 19 shows the design of the wire 101 with a spiral counter-rotating conical tip 105. At the first end 121 and the second end 122, the wire spirals conically in different opposite directions, with the middle of the wire then having a finger-like loop 122. The first and second ends of the wire 101 have a length from about 10 mm to about 50 mm with a referred length from about 15 mm to about 30 mm. the finger-like loop 122 has a length of from about 5 mm to about 30 mm with a preferred length from about 7 mm to about 15 mm. it should be appreciated, however, that the length of the loop 122 and the first and second ends is dependent on the size of the blood vessel where the device is used. The counter rotation of the wire has sever unique properties. During the initial deployment, the first end 120 is deployed distally to the thrombus and prevents distal migration of the thrombus. With further deployment, it creates a space between the first and second ends for the thrombus to fit into. At the place of change of direction, a loop 122 is formed. The finger-like loop 122 in the middle is designed to be positioned along the inside of the vessel wall 100 and mechanically scrape or remove the thrombus 102 or 108 from the vessel wall as the proximal deployment occurs, effectively encircling the thrombus 102 or 108 within the wire 105. This could be very useful for removing very chronic thrombi that are adherent to blood vessel walls. If the thrombus 102 or 108 is not encircled during deployment, the central finder-like loop 122 can be rotated, with the rotation of the wire 105 itself, to scrape the thrombus 102 or 108 off the vessel wall 100 and entrain it into the middle of the spiraled wired 105. Finally, during retrieval, the conical first and second ends of the spiral wire effectively form a capture spiral to retain the thrombus 102 or 108 during the removal. The wire 101 is also designed to allow it to easily be retracted into the funnel 106 and prevent distal embolization of the thrombus 102 or 108 during the terminal stages of thrombus retrieval. The conical shape of the first and second ends is designed, to unwind during retrieval into the sheath.

The basket 103, wire 104, wire 101 with a spiral counter-rotating conical tip 105 are withdrawn in the blood vessel capturing (snaring) the thrombus 102 or 108 until these components are nested in the deployed funnel 106. The funnel 106 (encompassing the basket 103, wire 104, wire 101 with a spiral counter-rotating conical tip 105, and thrombus 102 or 108) is retrieved through the main sheath 107. A continuous aspiration can be applied through a (large) side port with a male-threaded end (18-18 Fr) connected to an aspiration syringe with: a female-threaded end (16-18 Fr) during the retrieval of funnel 106. Once the thrombus is retrieved, the funnel 106 is collapsed and withdrawn within the main sheath 107 and the thrombus 102 or 108 is removed.

The basket 103 and funnel 106 are made of braided superelastic nitinol wires shape-set in a way to have an open cell design, while being in a deployable state, without the need for any membrane or filament. This allows for maintenance of blood flow during the deployment, operation, and retrieval.

Figure 21:
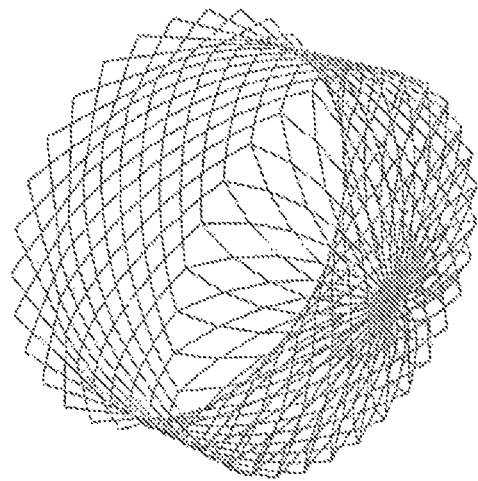
FIG. 21 is a perspective view of a part of the device.

The braided superelastic nitinol wires are shape-set in a way to allow for the basket 103 to change its shape by allowing the opening in the basket to fold backward, see FIG. 21. By folding backwards, the opening of the basket engages the thrombus and can assist in removing the thrombus from the wall of the blood vessel. The longer funnel 106 with wider opening diameter creates more surface area for contact with thrombus at the extension 109 at the opening and this is beneficial in capturing the emboli. This design results in a strengthened funnel structure and an increased maximum dragging force, while remaining atraumatic, during thrombus removal.

The basket 103, funnel 106, and wire 101 with a spiral counter-rotating conical tips 105 can have differential surfaces. These components can have an outside that is finely polished and an inside that is either rough, or has microscopic surfaces, like shark skin, that unidirectionally latches onto objects, like thrombus 102 or 108, to retain the object as is being pulled back, against the current of blood, to be retained into a sheath 107 catheter or other devices.

In alternative preferred embodiments, the basket 103, funnel 106, and wire 101 with a spiral counter-rotating conical tip 105 may be coated with biologic products that specifically adhere to the materials we desire to retrieve (thrombus). As an example, the Fab fragment of anti-bodies can be used, specifically directed against human proteins such as fibrin, activated platelet receptors (IIb/IIIa), or other materials found in thrombi. These antibody fragments attached to the retrieval devices will form a biologic locking mechanism to hold the thrombus 102 or 106 to the basket 103, funnel 106 and wire 101, selectively retrieving only the desired biologic products from the body.

Figure 20:
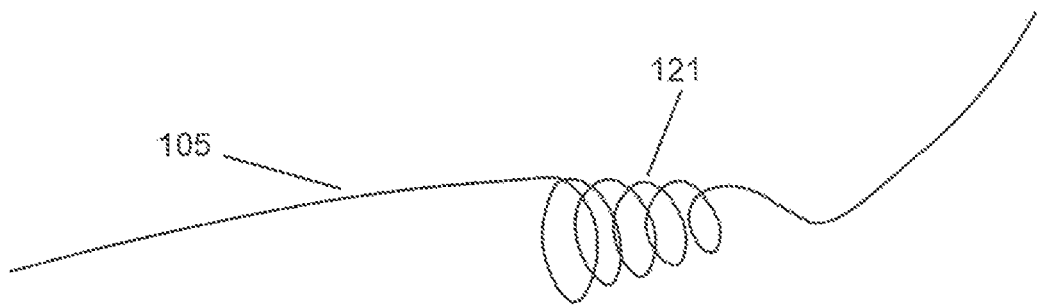
FIG. 20 is a side elevational view of a part of the device.

Another shape of the wire with a spiral counter-rotating conical tip is shown in FIG. 20. The wire 130 has a first end 133 and a second end 135. A conical section 137 is disposed on the wire between the first end and the second end. The conical section is disposed to engage and retrieve a thrombus with the basket 103 and funnel 106 as previously described. This is a simpler structure for the wire where it is not necessary to have two counter rotating sections. The shape and size of the single conical section 137 is the same as the previously described conical sections on the first and second ends of the wire 101.

FIG. 22 shows a schematic representation of the design of the needed mandrill to make the spiral counter-rotating conical tip 105. The needed mandrill consists of two parts, right and left that can be assembled together. The superelastic nitinol wire 105 is then inserted from one end through the center hole and guided through the cortical grooves all the way to the second center hole at the other end. Finally, the wire 105 is constrained and shape set into the desired shape and dimensions.

Figure 30:
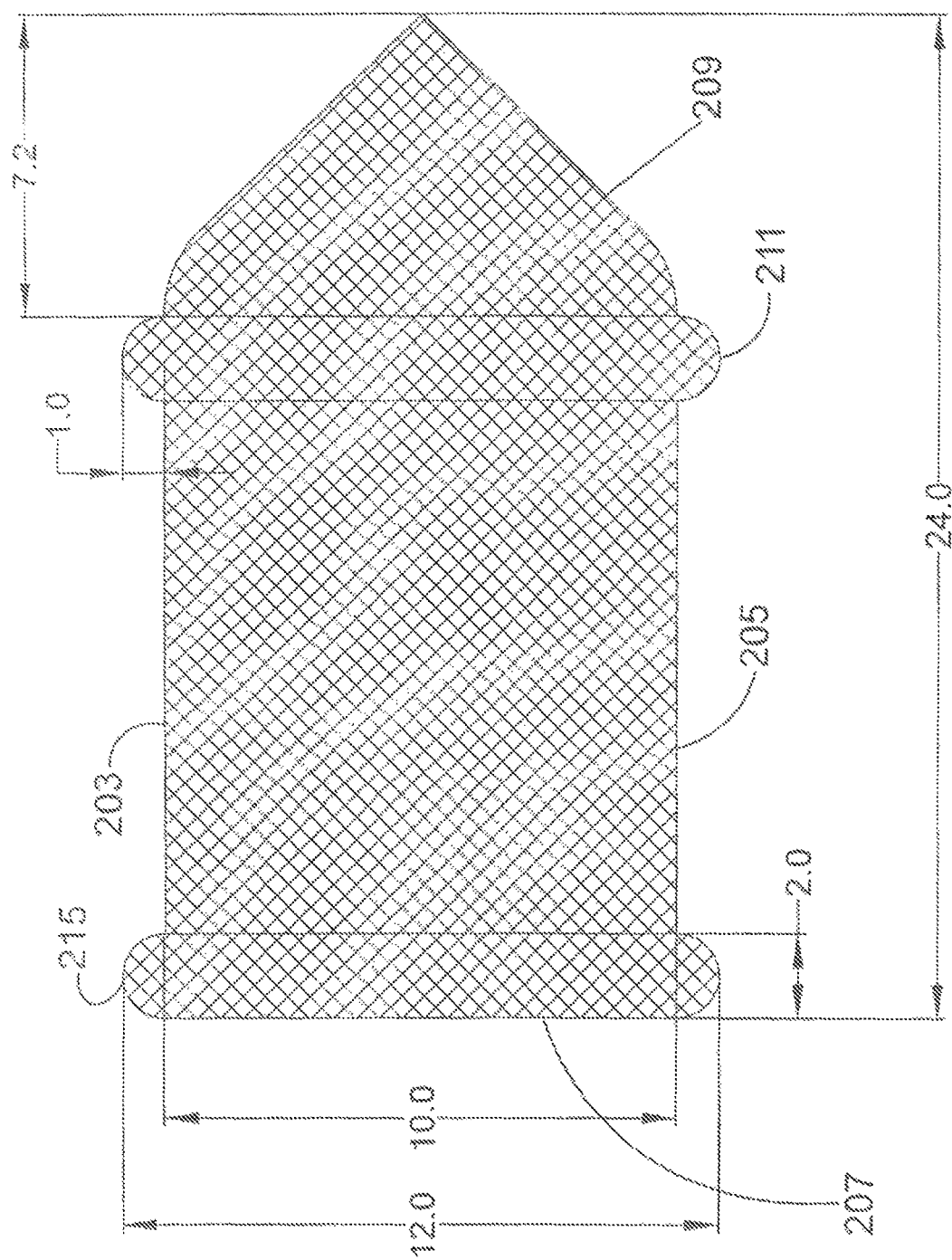
FIG. 30 is a partial side elevational view.

FIG. 30 shows another configuration for a basket that can be used to remove a thrombus from a blood vessel. The basket 203 has a cylindrical section 205 having an opening 207 and a conical section 209 that is joined to the end of the cylindrical section 205 that is spaced apart from the opening 207. The conical section 209 functions to close the cylindrical section 205. A raised rib 211 is formed in the cylindrical section 205 adjacent the end where the conical section 209 is connected to the cylindrical section 205. A raised rib 215 is located on the cylindrical section 205 adjacent the opening 207. The basket 203 is made of a braided superelastic nitinol wires that are shape-set as previously described in this application. The ribs 211 and 215 are reinforcing elements that provide additional structural rigidity for the basket 203. In particular, a rib 215 assists in maintaining the opening 207 in a desired fully extended position while the basket 203 is used to remove and collect the thrombus from a blood vessel. The rib 211 provides structural rigidity for a end of the basket 203 that is spaced apart from the opening 207. The rib 211 and the rib 215 act to keep the basket 203 in a fully extended position as it is pulled along the blood vessel towards the funnel 106 which is the other element of the thrombus capture device. The fully extended orientation for the basket 203 assist in positioning the basket where it can engage as completely as possible the thrombus and remove the thrombus from the walls of the blood vessel. The basket is used in the same manner as the basket 103 to remove a thrombus.

Figure 31:
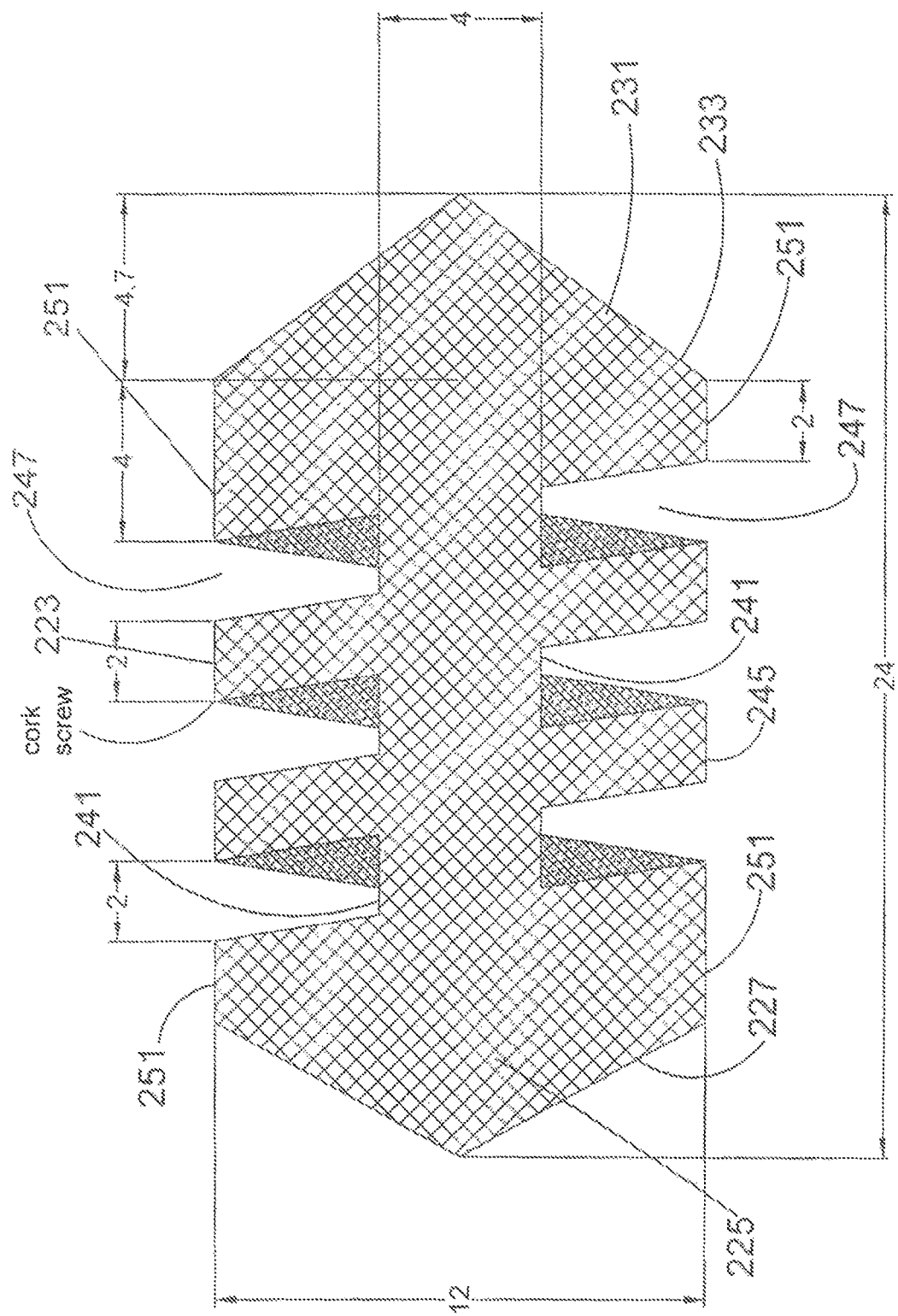
FIG. 31 is a partial side elevational view.

FIG. 31 shows another feature of the invention where a plug 223 can be used in place of the basket 103, 203 to assist in removing the thrombus form a blood vessel. The plug 223 is attached to the wire 104 or wire 101 with the spiral counter-rotating conical tip 105 as previously discussed in this application. The plug 223 is made of braided superelastic nitinol wires that are shaped-set in a way to have an open cell design, while in the deployed state, without the need for any membrane or filament as previously discussed in this application. The plug can be deployed in a compressed state and when the constraining sheath used to deliver the plug is removed the plug expands to its full extended shape set stage as shown in FIG. 31. The plug has a first conical end 225 located on the first end 227 and a second conical end 231 located on the second end 233 of the plug. A reinforcing member 241 extends along the longitudinal axis of a plug from the first conical end 225 to the second conical end 231. The reinforcing member 241 is positioned on each side of the plug 223. The reinforcing member has a height that is approximately one third of the diameter of the first and second conical sections. A spiral section 245 of braided superelastic nitinol wires extends from the first conical end 225 to the second conical end 231 of the plug 223. The spiral section 245 has a diameter that is substantially the same as the diameter of the first and second conical ends of the plug. The spiral section 245 creates a cylindrical spiral that extends from the first end 227 to the second end 233 of the plug 223. Openings 247 are positioned between the spiral sections 245 and the openings provide access to the interior of the plug 223. The spiral sections 245 form a cylindrical band 251 that engage the outer diameter of the first and second conical sections located on the first and second ends respectively of the plug 223.

The plug 223 is deployed in the blood vessel in the same manner as the basket 103, 203 on the distal side of the thrombus as previously described: Once the plug is in the desired location it is deployed by removing the delivery sheath and allowing the plug to expand due to the shape-set characteristics of the plug. The plug is then advanced towards the thrombus and the funnel 106. The first conical end 227 engages the thrombus and advances it towards the funnel 106. The cylindrical band 251 adjacent the first cylindrical section 227 is designed to be adjacent the wall of the blood vessel and to retain the thrombus adjacent the first end 225 of the plug 223. If the thrombus is secured to the walls of the blood vessel, the cylindrical bands 251 will abrade against the thrombus and, hopefully, break the thrombus free from the walls of the blood vessel. Pieces of the thrombus that are removed from the walls of the blood vessel by the cylindrical bands 261 will fall into the openings 247 between the spiral sections 245 and enter the interior of the plug 223. If the cylindrical bands 251 do not remove all of the portions of the thrombus that are attached to the walls of the blood vessel, the following spiral section 245 will engage and, hopefully, displace the thrombus from the walls of the blood vessel. Again, the displaced pieces of the thrombus can pass through the openings 247 into the interior of the plug 223. Pieces from the thrombus that enter the plug 223 from the openings 247 will be retained in the plug by the spiral sections 245 and the walls of the blood vessel. The pieces of the thrombus that are so dislodged and positioned in the interior of the plug 223 will also be confined by the second cylindrical section 231 on the second end 233 of the plug. The plug 223 will be advanced into the funnel 106 in the manner previously described so that the thrombus will be between the plug 223 and the funnel 106. The cylindrical section 109 on the funnel 106 has a length that is at least as long as the length of the plug 223 so that the plug 223 will be fully enclosed within the funnel 106.

To assist in positioning the basket and funnel in the blood vessel, the superelastic material can have a shape memory that is dependent on the temperature of the material. The superelastic material can be maintained in a compressed state at a lower temperature, such as the temperature in an operating room, and then expend to its shape set expanded shape at a higher temperature, such as the temperature on the interior of a human body. The temperature shape memory can be designed for the nitinol superelastic material and be part of the shape setting process for the funnel, basket and wires used to remove a thrombus. The shape memory feature assists in having the components inserted into the body of the patient stay in a compressed state until the components are deployed from the delivery sheath. Once the components are deployed, the components are subject to the higher body temperature and expand to the desired expanded shape set orientation.

The principle and mode of operation of this invention have been explained and illustrated in its preferred embodiments. However, it must be understood that this invention may be practiced otherwise than as specifically explained and illustrated without departing from its spirit or scope.

We claim:

1. An apparatus for conducting a thrombectomy in a blood vessel of a patient comprising:
    an expandable basket designed for positioning in the blood vessel on a distal side of or adjacent to the thrombus, the expandable basket configured to expand once it is in position on the distal side of or adjacent to the thrombus, the expandable basket made from a superelastic or a shape memory material, having a mesh pattern that can retain the thrombus;
    a guide wire connected to the expandable basket for positioning the expandable basket in position on the distal side of or adjacent to the thrombus and for removing the expandable basket from the blood vessel; and
    an expandable funnel designed for positioning in the blood vessel on a proximal side of the thrombus, the expandable funnel having a cylindrical section, the expandable funnel configured to expand once it is in position on the proximal side of the thrombus with an open side of the expandable funnel facing the thrombus, the cylindrical section being designed to engage the wall of the blood vessel, the expandable funnel made from a superelastic or shape memory material, having a mesh pattern that can retain the thrombus, the apparatus having a deployed state wherein the expandable basket and expandable funnel expand and engage an internal wall of the blood vessel and a delivery state wherein the expandable basket and expandable funnel have a contracted configuration to allow insertion in the blood vessel within a delivery sheath, the expandable basket being designed to fit within the cylindrical section of the expandable funnel when the expandable basket is advanced towards the expandable funnel by the guide wire to remove the thrombus, the expandable funnel designed to encircle and constrain the thrombus during a removal process as it is withdrawn into an aspiration catheter, the apparatus having the ability to change shape and diameter as it is withdrawn into the aspiration catheter;
    wherein the expandable basket is a plug having a first conical end located on a first end and a second conical end located on a second end, wherein spiral sections extend from the first conical end to the second conical end, the spiral sections forming a cylindrical band that has a diameter substantially the same as a diameter of the first and second conical ends, and a reinforcing member extending parallel to a longitudinal axis of the plug from the first conical end to the second conical end, wherein the reinforcing member has a height that is approximately one third of the diameter of the first and second conical ends, wherein openings are positioned between the spiral sections, the openings being disposed to allow pieces from the thrombus to pass through the openings and into an interior of the plug.

2. The apparatus of claim 1 wherein a wire with a spiral orientation extends between the expandable basket and the expandable funnel, the spiral orientation of the wire being designed to engage the thrombus to assist in positioning the thrombus in a desired location for removal.

3. The apparatus of claim 2 wherein the wire has a first spiral section and a second spiral section, the first and second spiral sections having opposing spiral orientations.

4. The apparatus of claim 3 wherein an offset section is positioned between the first and second spiral sections, the offset section extending outwardly and being disposed to engage the wall of the blood vessel when the wire is rotated whereby the offset section can assist in dislodging the thrombus from the wall of the blood vessel.

5. The apparatus of claim 4 wherein the offset section has a length from about 5 mm to about 30 mm.

6. The apparatus of claim 4 wherein each of the first and second spiral sections has a length from about 10 mm to about 50 mm.

7. The apparatus of claim 3, the openings of the plug being disposed to allow pieces from the thrombus to pass through the openings of the plug and into an interior of the plug.

8. The apparatus of claim 1 wherein the cylindrical section has a length from about 5 mm to about 20 mm.

9. The apparatus of claim 1 wherein the cylindrical section has a length from about 15 mm to about 50 mm.

10. The apparatus of claim 1, wherein the cylindrical section has a length that is at least as long as a length of the plug.

11. The apparatus of claim 1, wherein the reinforcing member is integrally formed with the first conical end and the second conical end.

12. An apparatus for conducting a thrombectomy in a blood vessel of a patient comprising:
    an expandable basket made from a superelastic or a shape memory material, wherein the expandable basket has a mesh pattern;
    a guide wire connected to the expandable basket; and
    an expandable funnel connected to the guide wire, wherein the expandable funnel is made from a superelastic or shape memory material and has a mesh pattern, wherein the expandable funnel comprises a cylindrical section;
    wherein the apparatus has a deployed state wherein the expandable basket and the expandable funnel have an expanded configuration, and a delivery state wherein the expandable basket and the expandable funnel have a contracted configuration;
    wherein the expandable basket in the contracted configuration fits within the cylindrical section of the expandable funnel; and
    wherein the expandable basket is a plug having a first conical end located on a first end and a second conical end located on a second end, wherein spiral sections extend from the first conical end to the second conical end, the spiral sections forming a cylindrical band that engages an outer diameter of the first and second conical ends, and a reinforcing member extending parallel to a longitudinal axis of the plug from the first conical end to the second conical end, wherein the reinforcing member has a height that is approximately one third of the outer diameter of the first and second conical ends, wherein openings are positioned between the spiral sections.

13. The apparatus of claim 12, wherein the cylindrical section has a length that is at least as long as a length of the plug.

14. The apparatus of claim 12, wherein the reinforcing member is integrally formed with the first conical end and the second conical end.

\* \* \* \* \*